United States Patent [19]

Hirota et al.

[11] Patent Number: 4,876,034
[45] Date of Patent: Oct. 24, 1989

[54] SECONDARY AMIDOAMINO ACID BASED DETERGENT COMPOSITION

[75] Inventors: Hajime Hirota, Tokyo; Hidekazu Ogino, Koutoubashi; Sahoko Igarashi, Tokyo; Kohshiro Sotoya, Wakayama, all of Japan

[73] Assignee: Kao Corporation, Tokyo, Japan

[21] Appl. No.: 114,201

[22] Filed: Oct. 29, 1987

[30] Foreign Application Priority Data

Nov. 18, 1986 [JP] Japan .................................. 61-274927
Dec. 24, 1986 [JP] Japan .................................. 61-310431

[51] Int. Cl.⁴ .......................... C11D 1/10; C11D 1/88
[52] U.S. Cl. ............................... 252/546; 252/174.23; 252/DIG. 2; 252/DIG. 14; 252/DIG. 13
[58] Field of Search ................. 252/546, 544, 174.23, 252/DIG. 2, DIG. 13

[56] References Cited

U.S. PATENT DOCUMENTS

| | | | |
|---|---|---|---|
| 2,961,451 | 11/1960 | Keough et al. | 260/404.5 |
| 3,055,836 | 9/1962 | Masci et al. | 252/545 |
| 4,381,259 | 4/1983 | Homma et al. | 252/542 |
| 4,578,216 | 3/1986 | Fujii et al. | 252/542 |

FOREIGN PATENT DOCUMENTS

| | | |
|---|---|---|
| 1042811 | 11/1958 | Fed. Rep. of Germany . |
| 1049036 | 1/1959 | Fed. Rep. of Germany . |
| 58708 | 5/1977 | Japan . |
| 336 | 1/1980 | Japan . |
| 25436 | 2/1980 | Japan . |
| 25458 | 2/1980 | Japan . |
| 16599 | 2/1981 | Japan . |
| 168796 | 9/1985 | Japan . |

OTHER PUBLICATIONS

Patent Abstracts of Japan, vol. 10, No. 49, (Feb. 26, 1986).
Chemical Abstracts, vol. 104, No. 18, p. 133, (May 1986), 151315y.
Chemical Abstracts, vol. 104, No. 18, p. 133, (May 1986), 151316z.

Primary Examiner—Prince E. Willis
Attorney, Agent, or Firm—Oblon, Spivak, McClelland, Maier & Neustadt

[57]    ABSTRACT

A novel detergent composition comprising as a main detergent active ingredient a secondary amidoamino acid or its salts of the following general formula (I):

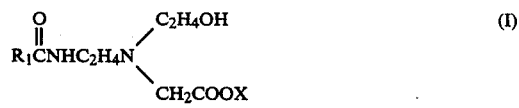

The detergent composition has low irritativeness and good detergency, so that it is appropriately used as hair and skin detergents for babies, dish wash detergents and the like.

3 Claims, 1 Drawing Sheet

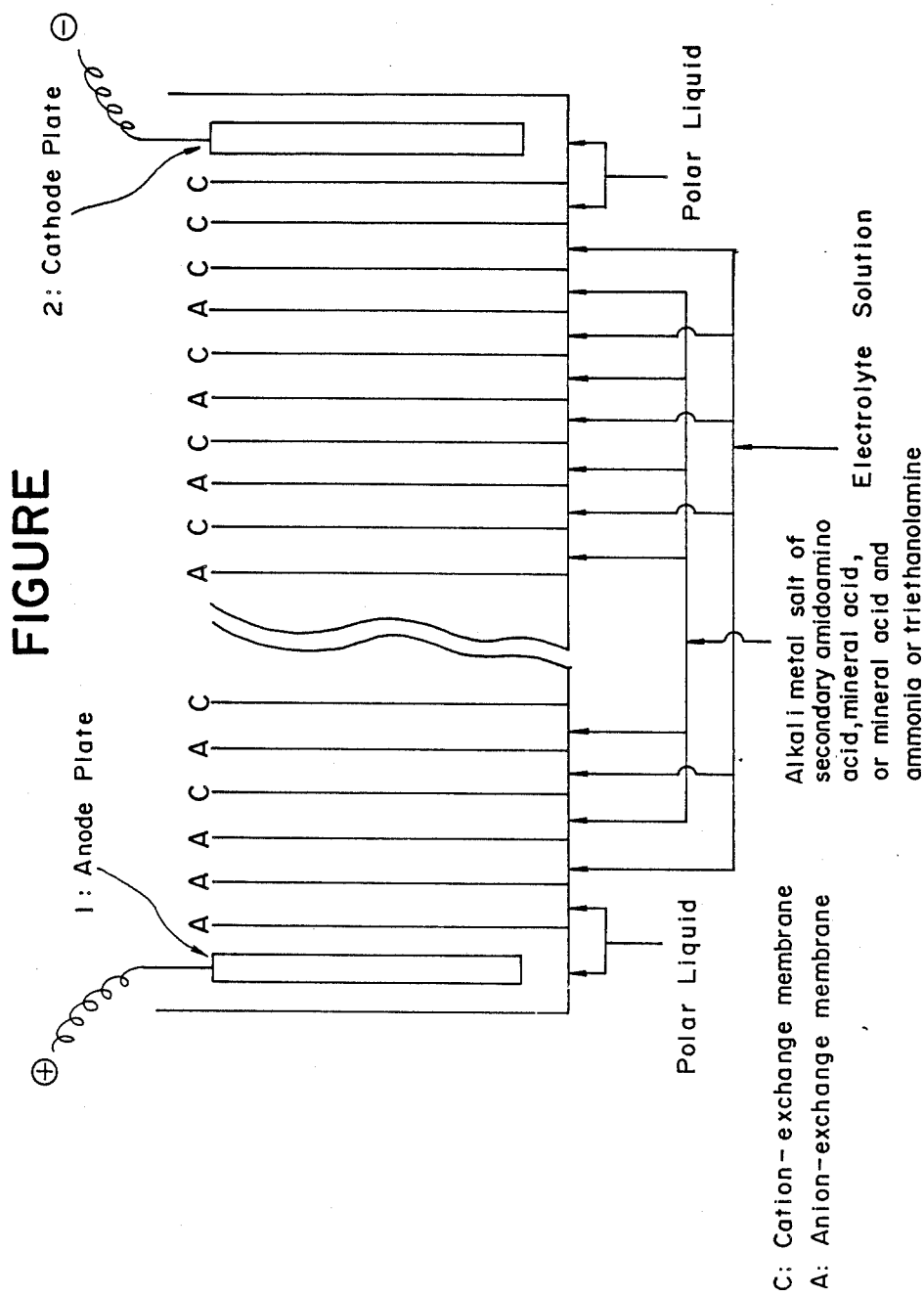

SECONDARY AMIDOAMINO ACID BASED DETERGENT COMPOSITION

BACKGROUND OF THE INVENTION

1. Field of the Invention

This invention relates to detergent compositions and more particularly, to detergent compositions which have good lathering ability and detergency and are mild to the skin, hair and eyes.

2. Description of the Prior Art

The sodium salts of secondary amidoamino acids of the following general formula (I') called imidazoline-type amphoteric surface active agents have been hithertofore used as a main detergent active ingredient such as of baby shampoos or bathing agents because of the low irritativeness against the skin and eyes,

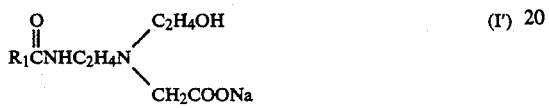

in which $R_1$ represents an alkyl group, a hydroxyalkyl group, an aralkyl group or an alkenyl group each having from 7 to 23 carbon atoms.

However, this sodium salt of the secondary amidoamino acid is not always better than ordinary anionic surface active agents such as alkylsulfates and alkyl ether sulfates with respect to detergency and lathering ability, and have not been widely used as a detergent.

The sodium salt of the secondary amidoamino acid has large amounts of water-soluble inorganic salts such as common salt by-produced at the time of the preparation, so that when it is used as a base of liquid shampoos, it becomes difficult to thicken or condition of the shampoo. In order to permit the liquid to be thickened or conditioned, various water-soluble polymers are ordinarily used. Most of these polymers are insoluble in a concentrated salt solution, so that it is difficult to formulate into aqueous liquid detergents together with known sodium salts of secondary amidoamino acids containing large amounts of inorganic salts.

SUMMARY OF THE INVENTION

Under these circumstances, the present inventors made intensive studies and, as a result, found that when the above salt is converted into a secondary amidoamino acid or its salt (an ammonium salt or a triethanolamine salt) of the following general formula

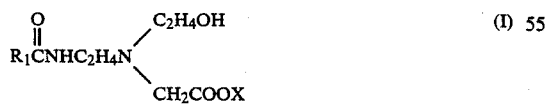

in which $R_1$ represents an alkyl group, a hydroxyalkyl group, an aralkyl group or an alkenyl group each having from 7 to 23 carbon atoms, and X represents a hydrogen atom, an ammonium ion, or a triethanolamine ion, the lathering ability and detergency can be improved without impeding the low irritativeness. Moreover, when the by-produced water-soluble inorganic salts are removed (hereinafter referred to as desalting), water-soluble polymers may be formulated without troubles. The present invention was accomplished based on the above finding.

In accordance with one embodiment of the invention, there is provided a detergent composition which comprises as a main detergent active ingredient a secondary amidoamino acid or its salt of the formula (I).

According to another embodiment of the invention, there is also provided a liquid detergent composition which comprises from 1 to 45 wt.% of a secondary amidoamino acid or its salt of the formula (I) and from 0.05 to 10 wt% of a water-soluble polymer which is insoluble in a concentrated salt solution, with a content of water-soluble inorganic salts being not larger than 1 wt%.

BRIEF DESCRIPTION OF THE DRAWING

The sole FIGURE is a schematic view illustrating one example of an electrodialysis vessel used in synthetic examples.

DETAILED DESCRIPTION OF THE INVENTION AND PREFERRED EMBODIMENTS

The secondary amidoamino acid or its salt of the general formula (I) used in the present invention is prepared according to the following procedure.

An alkylimidazoline of the formula (III) or an amidoamine of the formula (IV) which is a ring-opened compound of the alkylimidazoline is reacted with a monohaloacetic acid such as sodium monochloroacetic acid or its salt in the presence of an alkali to obtain an alkali metal salt such as a sodium salt of a secondary amidoamino acid of the above-indicated formula (I'). During the procedure, inorganic salts such as alkali metal halides are by-produced in large amounts.

in which $R_1$ has the same meaning as defined above.

When a mineral acid is added to the thus obtained mixed solution of the alkali metal salt of the secondary amidoamino acid and the inorganic salts in amounts equimolar to or larger than the secondary amidoamino acid and subjected to electrodialysis, the acid-type secondary amidoamino acid [in formula (I), X=H] is obtained with the content of the inorganic salts being small. When the acid-type secondary amidoamino acid is neutralized with ammonia or triethanolamine, there is obtained an ammonium salt or a triethanolamine salt of the secondary amidoamino acid.

After the addition of a mineral acid to the mixed solution of the alkali metal salt of the secondary amidoamino acid and the inorganic salts in amounts equimolar to or larger than the secondary amidoamino acid, the mixture is subjected to electrodialysis while dropping equimolar or larger amounts of ammonia or triethanolamine. As a result, an ammonium salt or a triethanolamine salt of the secondary amidoamino acid of the formula (I) can be directly obtained in a reduced content of the inorganic salts.

When the secondary amidoamino acid or its salt of the formula (I) used in the present invention has a lower content of the water-soluble inorganic salts, ingredients such as a water-soluble polymer are more likely to be formulated in liquid detergents, or the shape retention is more likely to be controlled in solid detergents. Accordingly, the content of the water-soluble inorganic salts should preferably be not larger than 0.2 moles per 100 g of the acid-type secondary amidoamino acid (calculated as the acid-type amidoamino acid when the salt is used). The content of the inorganic salts can be lowered by increasing the time of the electrodialysis.

In the formula (I), the acyl groups, $R_1CO$, can be derived from a linear or branched saturated or unsaturated aliphatic acid having from 8 to 24 carbon atoms. The most preferable aliphatic acid is lauric acid or coconut oil fatty acid.

In the practice of the invention, water-soluble polymers which are insoluble in a concentrated salt solution are those polymers which are insoluble in an aqueous 10 wt% salt solution and which are added in order to increase the viscosity or improve finish touch. Examples of such polymers include the following cationic polymers, anionic polymers, nonionic polymers and amphoteric polymers.

Cationic Polymers:

These polymers are left on the skin, hair or fibers by adsorption and can improve the finish touch after washing.

(I) Cationic cellulose derivatives

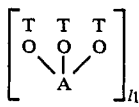
(1)

in which A represents a residue of an anhydroglucose unit, $l_1$ is an integer of from 50 to 20,000, and each T represents a substituent of the following general formula (2)

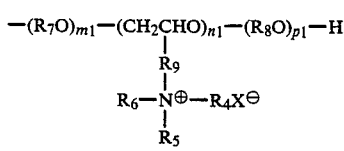
(2)

in which
$R_7$, $R_8$: an alkylene group having 2 or 3 carbon atoms,
$m_1$: an integer of from 0 to 10,
$n_1$: an integer of from 0 to 3,
$p_1$: an integer of from 0 to 10,
$R_9$: an alkylene or hydrooxyalkylene group having from 1 to 3 carbon atoms,
$R_4$, $R_5$, $R_6$: they may be the same or different and represent an alkyl group having up to 10 carbon atoms, an aryl group or an aralkyl group, or may form a heterocyclic ring containing the nitrogen atom in the formula, and
X: an anionic group such as chlorine, bromine, iodine, sulfate, sulfonate, methylsulfate, phosphate, nitrate or the like.

The degree of substitution of the cation in the cationic cellulose is in the range of from 0.01 to 1, or the average value of $n_1$ per anhydroglucose unit is in the range of from 0.01 to 1, preferably from 0.02 to 0.5. The total of $m_1+p_1$ is from 1 to 3 on the average. The degree of the substitution less than 0.01 is not satisfactory. On the other hand, it may be over 1 but is favorably below 1, inclusive, in view of the reactivity. The molecular weight of the cationic cellulose is between about 100,000 and 3,000,000, (II) Cationic starch

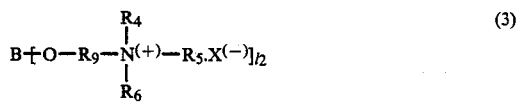
(3)

in which
B: a starch residue,
$l_2$: a positive integer, and
$R_{4-6}$, $R_9$, X: the same meanings as defined before, respectively.

The degree of substitution of the cation in the cationic starch is in the range of from 0.01 to 1, or the number of the cationic group per anhydroglucose unit is from 0.01 to 1, preferably from 0.02 to 0.5. With the degree of substitution less than 0.01, satisfactory effects cannot be obtained. The degree of substitution may be over 1 but is favorably not larger than 1 in view of the yield of the reaction.

(III) Diallyl quaternary ammonium salt/acrylamide copolymers

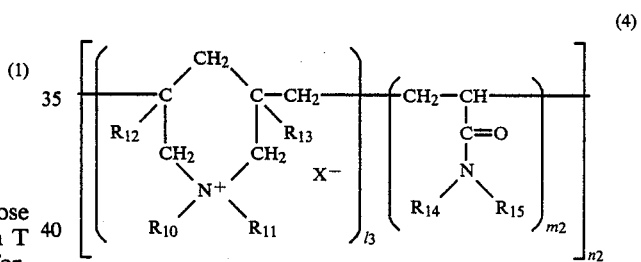
(4)

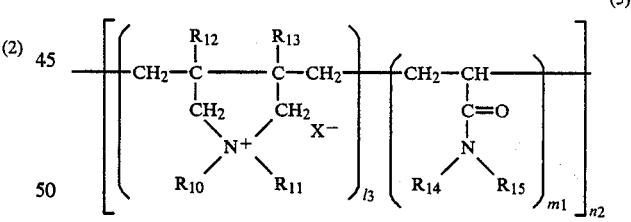
(5)

In the formulae (4) and (5),
$R_{10}$, $R_{11}$: they may be the same or different and represent hydrogen, an alkyl group having from 1 to 18 carbon atoms, a phenyl group, an aryl group, a hydroxyalkyl group, an amidoalkyl group, a cyanoalkyl group, an alkoxyalkyl group, or a carboalkoxyalkyl group,
$R_{12}$, $R_{13}$, $R_{14}$, $R_{15}$: they may be the same or different and represent hydrogen, a lower alkyl group having from 1 to 3 carbon atoms, or a phenyl group,
$l_3$: an integer of from 1 to 50,
$m_2$: an integer of from 1 to 50,
$n_2$: an integer of from 150 to 8000, and
X: the same meaning as defined before.

The molecular weight of the diallyl quaternary ammonium salt/acrylamide copolymer is in the range of from about 30,000 to 2,000,000, preferably from 100,000 to 1,000,000.

(IV) Quaternarized polyvinylpyrrolidone derivatives

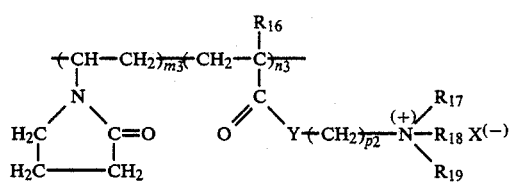

in which, $R_{16}$: a hydrogen atom or an alkyl group having from 1 to 3 carbon atoms, $R_{17}$, $R_{18}$, $R_{19}$: they may be the same or different and represent a hydrogen atom, an alkyl group, a hydroxyalkyl group, an amidoalkyl group, a cyanoalkyl group, an alkoxyalkyl group, or a carboalkoxyalkyl group, each having from 1 to 4 carbon atoms, Y: an oxygen atom or an NH group in the amido bond, X: the same meaning as defined before, $p_2$: an integer of from 1 to 10, and $m_3+n_3$: an integer of from 20 to 8000.

The molecular weight of this derivative is in the range of from 10,000 to 2,000,000, preferably from 50,000 to 1,500,000.

The content of the cationic nitrogen derived from the cationic polymer containing in the vinyl polymer is in the range of from 0.004 to 0.2 wt%, preferably from 0.01 to 0.15 wt%, of the vinyl polymer. With a content less than 0.004 wt%, satisfactory effects cannot be obtained. Over 0.2 wt%, good properties may be obtained, but the vinyl polymer may suffer coloration with a poor economy.

(V) Polyglycol/polyamine condensates

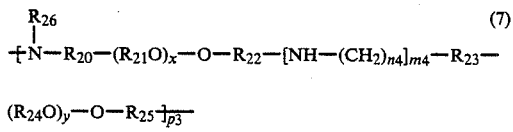

in which, $R_{20}$, $R_{22}$, $R_{23}$, $R_{25}$: a hydroxyalkylene group having from 2 to 4 carbon atoms, $R_{21}$, $R_{24}$: an alkylene group having from 2 to 3 carbon atoms, x, y: an integer of from 10 to 20, respectively, $m_4$: an integer of from 2 to 4, $n_4$: an integer of from 2 to 6, $p_3$: an integer of from 1 to 50, and $R_{26}$: a linear or branched alkyl group having from 6 to 20 carbon atoms.

(VI) Copolymers of adipic acid/dimethylaminohydroxypropyldiethylenetriamine (Calthaletin, available from Sandos Co., Ltd. of U.S.A.)

Anionic Polymers:

These polymers are chiefly used in order to increase the viscosity of liquid detergents.

(I) Alginic acid derivatives

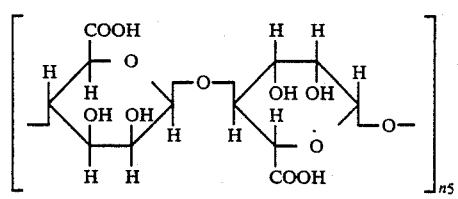

in which the site at the left side corresponds to D-mannronic acid and the site at the right side corresponds to L-gulironic acid, and thus the derivative is a heteropolysaccharide which is a copolymer of both acids, and $n_5$ is an integer of from 50 to 1000 with an average value being preferably from 100 to 300.

(II) Carboxymethyl cellulose derivatives

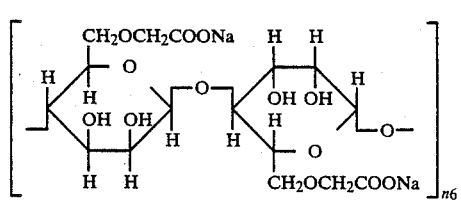

The degree of substitution of the ether in carboxymethyl cellulose is in the range of from 0.4 to 3.0, preferably from 0.5 to 1. $n_6$ is an integer of about 50 to 6000 with the average value of $n_6$ being preferably in the range of from 100 to 300.

(III) Acrylic acid derivatives

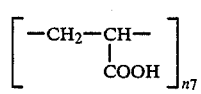

$n_7$ is in the range of about 200 to 100,000 and the average value of $n_7$ is preferably in the range of from 10,000 to 50,000. A favorable commercial cross-linked product is Carbopole (commercial name) of Goodrich Co., Ltd.

(IV) Carrageenan (V) Gum abrabic (VI) Gum tragacanth

Nonionic Polymers:

These polymers are chiefly used in order to increase liquid detergents (I) Cellulose derivatives

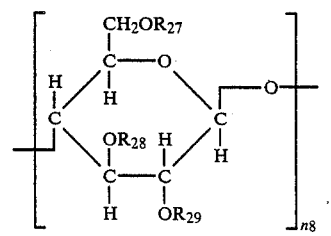

in the formula (10), $R_{27}$, $R_{28}$, $R_{29}$: a hydrogen atom, a group of $-(CH_2CH_2O)m_5-$ ($m_5$ is an integer of 1 to 5), $-CH_3$, or $-C_3H_6OH$, and $n_8$: an integer of 50 to 500.

Examples of the derivatives include hydroxyethyl cellulose, hydroxypropyl cellulose, hydroxypropyl methyl cellulose, methyl cellulose and the like.

Of these cellulose derivatives, hydroxyethyl cellulose is commercially sold under the name of Cellosize (UCC Inc.) or Natrosol (Hercules Inc.). The amount of added ethylene oxide per unit glucose residue is in the range of from 1.0 to 4.0, preferably from 1.8 to 3.0.

Methylcellulose is commercially available under the name of Kriminal MC (Henkel Co., Ltd.) and hydroxypropyl cellulose is available under the name of Crucel (Hercules Inc.), and hydroxypropylmethyl cellulose is available under the name of Metolose (Shinetsu Chem. Co., Ltd.) or Kriminal MHPC (Henkel Co., Ltd.). The content of the methoxy group in these methyl celluloses is in the range of from 10 to ;b 40 wt%, preferably from 20 to 30 wt%, and the content of the hydroxpropoxy group is in the range of from 1 to 20 wt%, preferably from 5 to 15 wt%.

(2) Polyvinyl alcohol derivatives
(3) Polyvinyl alkyl ether derivatives
(4) Polyethylene oxide derivatives Amphoteric polymers:

They are formulated in order to improve the finish touch after washing and include, for example, (1) copolymers of monomers having an nonionic group such as a carboxylic acid, sulfonic acid or the like, and monomers containing a basic nitrogen-containing group, (2) polymers of amphoteric monomers such as carboxybetaine-type monomers, (3) cationic polymers modified to introduce an anionic group such as a carboxyl group, a sulfonate group, and (4) anionic polymers modified to introduce a basic nitrogen-containing group. These amphoteric polymers have a charge density of anionic and cationic group, and if the ratio is close to 1:1, they becomes soluble in salts, so that it is preferred that a neutral hydrophilic group is appropriately introdued.

Preferred examples include the following polymers having a molecular weight of from 1,000 to 1,000,000.

(1) Polymers obtained by copolymerization of monomers obtained from vinyl compounds having a carboxyl group and selected from acrylic acid, methacrylic acid, maleic acid, and alpha-chloroacrylic acid, and substituted vinyl compounds having at least one basic nitrogen atom and selected fromdialkylaminoalkyl methacrylate or acrylate, dialkylaminoalkylmethacrylamide and acrylamide.

(2) Polymers having a site obtained from at least one basic copolymer, which are prepared from:
(a) at least one monomer selected from acrylamide and methacrylamide each substituted with an alkyl group at the nitrogen position;
(b) at least one acidic comonomer having one or a plurality of reactive carboxyl groups; and
(c) at least one basic comonomer such as primary, secondary, tertiary and quatenary amine-substituted esters of acrylic acid and methacrylic acid, quaternarized products of dimethylaminoethyl methacrylate with dimethylsulfate or diethylsulfate.

(3) Partially or fully cross-linked alkylated polyaminoamides obtained from polyamides of the following general formula

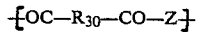

in which $R_{30}$ represents a divalent group obtained from a saturated dicarboxylic acid, a monofatty acid or a dicarboxylic acid having an ethylenically double bond, or an ester of a lower alcohol having from 1 to 6 carbon atoms and the above-indicated acid, or a group obtained by addition of the above-indicated acid and a bis(primary amine) or a bis(secondary amine), and Z represents a bis(primary amine), a mono or bis(secondary polyalkylene)polyamine group.

This polyamide is obtained by adding a crosslinking agent such as an epihalohydrin, a dieposidized product, a dianhydride and a bis-unsaturated derivative to a polyaminoamide in an amount of from 0.025 to 0.35 moles per unit amine group and causing acrylic acid, chloroacetic acid, an alkane/sultone or its salt to act on the resultant product.

(4) Polymers of the following formula having an amphoteric ion site

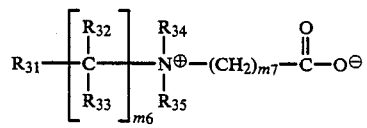

in which $R_{31}$ represents a polymerizable unsaturated group such as an acrylate, methacrylate, acrylamido or methacrylamido group, $m_6$ and $m_7$ are, respectively, an integer of from 1 to 3, $R_{32}$ and $R_{33}$, respectively, represents hydrogen atom, methyl, ethyl or propyl group, $R_{34}$ and $R_{35}$, respectively, a hydrogen atom, or an alkyl group having not larger than 10 carbon atoms as the total of $R_{34}$ and $R_{35}$.

The detergent composition of the invention may be formed into preparations, such as a solid, a liquid, a cream, a paste or an aerosol, comprising the secondary amidoamino acid or its salt of the formula (I) as a main detergent active ingredient.

The term "main detergent active ingredient" used herein is intended to mean an ingredient which is contained in the highest content among a plurality of detergent active ingredients and is favorably contained in an amount of not less than ⅓ of the total of all the detergent active ingredients, preferably not less than ½ and more preferably not less than ⅔ of the total. Other detergent active ingredients may include anionic, cationic, amphoteric and nonionic surface active agents.

In accordance with another embodiment of the invention, the liquid detergent composition is provided, which comprises from 1 to 45 wt% (hereinafter referred to simply as %), preferably from 2 to 20%, and more preferably from 5 to 15%, of the secondary amidoamino acid or its salt of the formula (I). A polymer which is soluble in water but insoluble in a concentrated salt solution is added in an amount of from 0.05 to 10%, preferably from 0.1 to 5%, more preferably from 0.2 to 2%.

In this case, the total amount of water-soluble inorganic salts derived from the secondary amidoamino acid or its salt and other surface active agents is generally not larger than 1%, preferably not larger than 0.5% and more preferably not larger than 0.1%. The content of the water-soluble inorganic salts can be reduced to an intended level by controlling an amount of the inorganic salts contained in the secondary amidoamino acid or its salt according to the amount of the inorganic salts derived from the other surface active agents.

The medium used is water, which is preferably used in the range of from 30 to 98% of the total composition.

The detergent composition of the invention may further comprise, aside from the above essential ingredients, ingredients used for ordinary detergents, such as surface active agents of alkylsulfates, alkyl ether sulfates, alkanolamines of higher fatty acids, N-acylamino acid salts, N-alkylamino acid salts, sulfosuccinic acid esters, and imidazoline amphoteric surface active agents, in amounts not impeding the properties of the composition.

Preferably, there is used a detergent composition which comprises from 5 to 35% of the secondary amidoamino acid or its salt of the formula (I) and from 1 to 17.5% of an alkylamino acid-type surface active agent of the following general formula (II)

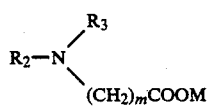
(II)

in which $R_2$ represents a saturated or unsaturated hydrocarbon group having from 8 to 20 carbon atoms, and $R_3$ represents hydrogen or a group of $-(CH_2)_m-COOM$ in which m is an integer of from 1 to 4 and M is a hydrogen atom, an alkali metal, an ammonium ion or an alkanolamine.

Examples of the compounds of the formula (II) include those of the formula in which $R_3$ is hydrogen, e.g. N-lauryl-beta-alanine, N-myristyl-beta-alanine, N-palmityl-beta-alanine and the like, and salts thereof, and those of the formula in which $R_3$ is $-(CH_2)_m-COOM$, e.g. N-lauryl-beta-iminodipropionic acid, N-myristyl-beta-iminodipropionic acid, N-palmityl-beta-iminodipropionic acid, N-lauryliminodiacetic acid, N-myristyliminodiacetic acid, N-palmitylimidinoacetic acid and salts thereof. Preferably, alkanolamine salts such as triethanolamine or ammonium salts are used because the above-indicated polymer, which is soluble in water but insoluble in a highly concentrated inorganic salt solution, can be formulated in an amount of from 0.05 to 10%.

The preferred amounts of the respective ingredients in the detergent composition are as follows: the amount of the secondary amidoamino acid or its salt of the formula (I) is in the range of from 10 to 30%; and the amount of the alkylamino acid-type surface active agent of the formula (II) is in the range of from 1 to 15%.

It should be noted that detergent compositions comprising an alkylamino acid-type surface active agent of the formula (II) and an amidoamino acid or its salts of the following formula (III) or (IV) are low in irritativeness against the skin and have good lathering ability and detergency, but are not better than the detergent compositions of the present invention

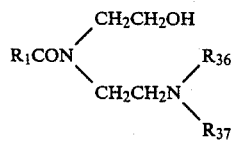
(III)

-continued $$R_1CONHCH_2CH_2 \diagdown ^{CH_2CH_2OH}_{CH_2CH_2COOM} \qquad (IV)$$

in which $R_{36}$ represeents a group of $-CH_2COOM$ or $-CH_2CH_2COOM$, $R_{37}$ represents a hydrogen atom or a group of $-CH_2COOM$ or $-CH_2CH_2COOM$, and $R_1$ and M have, respectively, the same meanings as defined before.

The detergent compositions of the invention may further comprise, if necessary, oils, perfumes, colorants, UV absorbers, humectants, hydrotropes, preservatives, antioxidants, and medical agents such as anti-dandruff agents, bactericides, antiinflammatories, vitamins and the like.

According to the invention, there can be provided detergents which have low irritativeness and good detergency. These detergents are appropriately used as hair and skin detergents for babies, wool or kitchen detergents for housewives who are liable to chap, or daily shampoos for those who wash the hair every day. Moreover, they are suitably used as beauty care shampoos or low irritativeness for those who are invariably brought into contact with shampoo over a long time professionally.

Synthetic examples and examples are described, which should not be construed as limiting the present invention.

SYMTHETIC EXAMPLE 1

A four-necked flask equipped with an agitator, a condenser, a dropping funnel and a thermometer was provided, in which 268 g (1 mol) of 1-hydroxyethyl-2-lauryl imidazoline, 90 g of water and 2 g of sodium hydroxide were placed and heated up to 80° C. while agitating, followed by continuing the agitation at the temperature for about 2 hours, thereby permitting the imidazoline to be ring-opened. Thereafter, a separately prepared solution of 233 g (2 mol) of sodium monochloroacetate and 2347.2 g of water was dropped into the flask in about 1 hour. During the dropping, the temperature of the solution was maintained at 70° to 80° C. Subsequently, 200 g of a 40% sodium hydroxide aqueous solution was dropped at the same temperature in 4 hours. After completion of the dropping, the reaction system was aged at a temperature of 75° to 80° C., thereby obtaining an about 12% aqueous solution of N-lauroyl-N'-2-hydroxyethyl-N'-sodium carboxymethylethylenediamine. After cooling of this solution, 213.8 g of 35% hydrochloric acid was dropped in about 3 hours. As a result, 3354 g of an aqueous 12% solution of N-lauroyl-N'-2-hydroxyethyl-N'-sodium carboxymethylethylenediamine hydrochloride of the following formula were obtained.

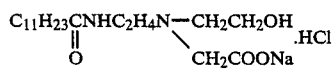

This solution is a light brown, viscous liquid and the pH of a 1% aqueous solution was found to be 2.5.

3354 g of the thus obtained aqueous solution was subjected to electrodialysis.

The electrodialysis was effected by a method in which, as shown in FIG. 1, a solution of N-lauroyl-N'-2- hydroxyethyl-N'-2-hydroxyethyl-N'-sodium carboxymethylethylenediamine hydrochloride was placed in each cell (organic matter cell) between an anion exchange membrane (A) and a cation exchange membrane (C), a 1% NaCl solution was placed in adjacent cells (electrolyte cells), and a 3% Glauber's salt solution was circulated as a polar liquid, to which a direct current was applied. The electrodialysis apparatus used in this synthetic example had 10 anion exchange membranes and 10 cation exchange membranes, each having an area of 0.02 m². The current used was an initial current density of 1.5 A/dm² and was applied for 15 hours. The final current density after 15 hours was 0.1 A/dm².

After completion of the electrodialysis, the water was completely removed by drying under reduced pressure, thereby obtaining white powder crystals. This product was confirmed to be N-lauroyl-N'-2-hydroxyethyl-N'-carboxymethylethylenediamine in view of the results of the amine value and the results of AV, IR and NMR analyses. The purity as an acid was 97% from the results of an analysis on Na and Cl and the content of sodium chloride was found to be 1.4 g (0.024 mol) per 100 g of N-lauroyl-N'-2-hydroxyethyl-N'-carboxymethylethylenediamine. The crystals were recrystallized from ethanol/acetone and subjected to an elemental analysis and identified as an intended acid of the following formula,

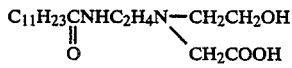

The results of the elemental analysis are shown below.

|   | Calculated | Found |
|---|---|---|
| C | 62.76% | 62.84% |
| H | 10.53 | 10.59 |
| N | 8.13 | 8.16 |
| O | 18.58 | 18.47 |

The resultant product has a content of sodium chloride of not larger than 0.12 g per 100 g of the acid.

This acid was dissolved in water to a concentration as high as possible, into which triethanolamine or a concentrated ammonia solution was dropped to a pH of 7.0, thereby obtaining an aqueous solution of a neutralized product for use in subsequent examples.

SYNTHETIC EXAMPLE 2

A four-necked flask equipped with an agitator, a condenser, a dropping funnel and a thermometer was provided, in which 268 g (1 mol) of 1-hydroxyethyl-2-lauryl imidazoline, 90 g of water and 2 g of sodium hydroxide were placed and heated up to 80° C. while agitating, followed by continuing the agitation at the temperature for about 2 hours, thereby permitting the imidazoline to be ring-opened. Thereafter, a separately prepared solution of 233 g (2 mol) of sodium monochloroacetate and 427.0 g of water was charged into the flask. While the temperature of the solution was maintained at 70° to 80° C., 200 g of a 40% sodium hydroxide aqueous solution was dropped at the same temperature in 4 hours. After completion of the dropping, the reaction system was aged at a temperature of 75° to 80° C., thereby obtaining an about 30% aqueous solution of N-lauroyl-N'-2-hydroxyethyl-N'-sodium carboxymethylethylenediamine. 149.2 g (1 mol) of triethanolamine was added to the solution and cooled. The resultant solution was a light brown liquid with a pH of about 9.

The thus obtained aqueous solution was subjected to electrodialysis.

The electrodialysis was effected by a method in which, as shown in FIG. 1, a mixed solution of N-lauroyl-N'-2-hydroxyethyl-N'-2-hydroxyethyl-N'-sodium carboxmethylethylenediamine and triethanolamine was placed in each cell (organic matter cell) between an anion exchange membrane (A) and a cation exchange membrane (C), a 1% NaCl solution was placed in adjacent cells (electrolyte cells), and a 3% Glauber's salt solution was circulated as a polar liquid, to which a direct current was applied. While 213.8 g (2.05 mol) of 35% HCl was uniformly added to the mixed solution in about 4 hours, the electrodialysis was effected.

The electrodialysis apparatus used in this synthetic example had 10 anion exchange membranes and 10 cation exchange membranes, each having an area of 0.02 m². The current used was an initial current density of 2 A/dm² and was applied for 12 hours. The final current density after 12 hours was 0.1 A/dm².

In this manner, a 35% solution of N-lauroyl-N'-2-hydroxyethyl-N'-triethanolaminocarboxymethylethylenediamine was obtained. The results of the analysis of the triethanolamine with Na and by liquid chromatography revealed that the counter ions were exchanged at 98%. Moreover, the analysis of Cl demonstrated that 1.43% (0.024 mol) was contained per 143 g (100 g as an acid) of N-lauroyl-N'-2-hydroxyethyl-N'-triethanolaminocarboxymethylethylenediamine. Part of the product was dried under reduced pressure and subjected to an IR analysis, revealing the formation of the above substance.

SYNTHETIC EXAMPLE 3

A four-necked flask equipped with an agitator, a condenser, a dropping funnel and a thermometer was provided, in which 268 g (1 mol) of 1-hydroxyethyl-2-lauryl imidazoline, 90 g of water and 2 g of sodium hydroxide were placed and heated up to 80° C. while agitating, followed by continuing the agitation at the temperatue for about 2 hours, thereby permitting the imidazoline to be ring-opened. Thereafter, a separately prepared solution of 233 g (2 mol) of sodium monochloroacetate and 427 g of water was charged into the flask. Subsequently, while the temperature of the solution was maintained at 70° to 80° C., 200 g of a 40% sodium hydroxide aqueous solution was dropped at the same temperature in 4 hours. After completion of the dropping, the reaction system was aged at a temperature 75° to 80° C., thereby obtaining an about 30% aqueous solution of N-lauroyl-N'-2-hydroxyethyl-N'-sodium carboxymethylethylenediamine.

The thus obtained solution was subjected to electrodialysis.

The electrodialysis was effected by a method in which, as shown in FIG. 1, a solution of N-lauroyl-N'-2-hydroxyethyl-N'-sodium carboxymethylethylenediamine was placed in each cell (organic matter cell) between an anion exchange membrane (A) and a cation exchange membrane (C), a 1% NaCl solution was placed in adjacent cells (electrolyte cells), and a 3% Glauber's salt solution was circulated as a polar liquid, to which a direct current was applied. The electrodialysis was effected while uniformly adding 535 g (2.0 mol) of 20% NH₄Cl to the mixed solution.

The electrodialysis apparatus used in this synthetic example had 10 anion exchange membranes and 10 cation exchange membranes, each having an area of 0.02 m². The current used was an initial current density of 2 A/dm² and was applied for 12 hours. The final current density after 12 hours was 0.1 A/dm².

In this manner, an about 20% solution of N-lauroyl-N'-2-hydroxyethyl-N'-ammoniocarboxymethylethylenediamine was obtained. In view of the analysis of Na and N in the product, the counter ions were found to be exchanged at 95%. The analysis of Cl revealed that NaCl was contained in an amount of 2.1% (0.036 mol) per 105 g (100 g as an acid) of N-lauroyl-N'-2-hydroxyethyl-N'-ammoniocarboxymethylethylenediamine.

Part of the resultant product was dried under reduced pressures and subjected to IR analysis to confirm that the product was the above-indicated substance.

EXAMPLE 1

The lathering ability, detergency and skin irritativeness of various detergents with the formulations shown in Table 1 were evaluated. The results are shown in Table 1.

The evaluation of the properties was effected as follows.

(1) Detergency test

A dirt having substantially the same composition as the sebum on the scalp but containing 2% of carbon black (12% of paraffin, 21% of wax esters, 26% of triglyceride, 32% of higher fatty acids, 5% of cholesterol, 2% of monoglyceride) was uniformly applied to a wool muslin having a size of 5 cm×5 cm and dried. This contaminated cloth was placed in an about 1000 ml stainless steel cylinder having 500 ml of a 3% detergent solution and shaked in a thermostatic chamber of 40° C. for 6 minutes, followed by rinsing with running water and drying for measurement of reflectance. The washing rate was obtained according to the following equation.

$$\text{Washing Rate} = \frac{\text{reflectance after washing} - \text{reflectance prior to washing}}{\text{reflectance of original cloth} - \text{reflectance prior to washing}}$$

Moreover, a residual sebum was extracted and quantitatively determined, and a defatting rate was similarly determined.

(2) Test method for skin irritativeness

The test method for skin irritativeness was effected by a sealing application method for men for 24 hours. More particularly, a sticking plaster impregnated with 0.1 ml of an aqueous solution of 0.2% of an effective surface active agent was applied to 20 persons for 24 hours. 24 hours after removal of the plaster, the irritativeness was judged. If a clear red spot appeared, it was judged as positive. The irritativeness was indicated by a positive rate.

(3) Lathering ability

A surface active agent was diluted with 4° DH hard water to a final concentration of an effective ingredient of 0.2% and the lathering ability was determined by a reverse agitation method. The measurement was effected using 0.5% lanolin at a temperature of 40° C. The results are indicated by an amount of lather (ml).

TABLE 1

| | | wt % Sample No. | | | |
|---|---|---|---|---|---|
| | | 1 | 2 | 3 | 4 |
| $C_{11}H_{23}CONHCH_2CH_2N\begin{smallmatrix}CH_2CH_2OH\\CH_2COOH\cdot N(CH_2CH_2OH)_3\end{smallmatrix}$ | (Synthetic Example 1) | 15 | | | |
| $C_{11}H_{23}CONHCH_2CH_2N\begin{smallmatrix}CH_2CH_2OH\\CH_2COOH\cdot NH_3\end{smallmatrix}$ | (Synthetic Example 1) | | 15 | | |
| $C_{12}H_{25}OSO_3H\cdot N(CH_2CH_2OH)_3$ | | | | 15 | |
| $C_{11}H_{23}CONHCH_2CH_2N\begin{smallmatrix}CH_2CH_2OH\\CH_2COO\cdot Na\end{smallmatrix}$ | (Synthetic Example 1) | | | | 15 |
| Ion-exchanged Water | | balance | → | → | → |
| Evaluation of Characteristic Properties: | | | | | |
| Skin irritativeness (positive rate, %) | | 3 | 3 | 42 | 6 |
| Lathering Strength (ml) | | 45 | 46 | 50 | 20 |
| Detergency (%) | | 85 | 82 | 58 | 60 |
| De-fatting Strength (%) | | 54 | 47 | 30 | 38 |

EXAMPLE 2

The comparison of amidoamino acid-type surface active agents with different structures is shown in Table 2.

TABLE 2

| | | | Sample No. | | | |
|---|---|---|---|---|---|---|
| | | | 5 | 6 | 7 | 8 |
| $C_{11}H_{23}CONHCH_2CH_2N\begin{smallmatrix}CH_2CH_2OH\\CH_2COOH \cdot N(CH_2CH_2OH)_3\end{smallmatrix}$ | (Synthetic Example 1) | | 15 | — | — | — |
| $C_{11}H_{23}CONHCH_2CH_2N\begin{smallmatrix}CH_2CH_2OH\\CH_2COOH \cdot NH_3\end{smallmatrix}$ | (Synthetic Example 1) | | — | 15 | — | — |
| $C_{11}H_{23}CON\begin{smallmatrix}CH_2CH_2OH\\CH_2CH_2N\begin{smallmatrix}CH_2COOH\\CH_2COOH \cdot NH_3\end{smallmatrix}\end{smallmatrix}$ | | | — | — | 15 | — |
| $C_{11}H_{23}CON\begin{smallmatrix}CH_2CH_2OH\\CH_2CH_2N\begin{smallmatrix}CH_2COOH \cdot N(CH_2CH_2OH)_3\\CH_2COOH \cdot N(CH_2CH_2OH)_3\end{smallmatrix}\end{smallmatrix}$ | | | — | — | — | 15 |
| Ion-exchanged Water | | | 85 | 85 | 85 | 85 |
| Resistance to Hard Water | | | o | o | x | x |
| Heat Stability | | | o | o | x | x |

(Note)
Hard Water Resistance: 1000° DH hard water was dropped into a solution of a surface active agent, whereupon a sample which immediately turned turbid was evaluated as "x", and a turbidity-free sample was evaluated as "o".
Heat Resistance: When stored as 50° C. for 3 months, a sample whose viscosity increased was evaluated as "x" and a sample which did not increase in viscosity was evaluated as "o".

EXAMPLE 3

Δ: semi-transparent liquid
x: precipitation

TABLE 3

| | | | wt % Sample No. | | | | | |
|---|---|---|---|---|---|---|---|---|
| | | | 9 | 10 | 11 | 12 | 13 | 14 |
| $C_{11}H_{23}CONHCH_2CH_2N\begin{smallmatrix}CH_2CH_2OH\\CH_2COOH \cdot N(CH_2CH_2OH)_3\end{smallmatrix}$ | (Synthetic Example 1) | | 14.3 | — | 14.3 | 14.3 | 14.3 | 14.3 |
| $C_{11}H_{23}CONHCH_2CH_2N\begin{smallmatrix}CH_2CH_2OH\\CH_2COOH \cdot NH_3\end{smallmatrix}$ | (Synthetic Example 1) | | — | 10.5 | — | — | — | — |
| NaCl | | | 0.33 | 0.66 | 0.99 | 1.32 | 1.65 | 3.30 |
| Methylcellulose | | | 1 | 1 | 1 | 1 | 1 | 1 |
| Ion-exchanged Water | | | balance | balance | balance | balance | balance | balance |
| Behavior of Dissolution | | | — | — | o | Δ | x | x |
| Low-temperature Stability | | | o | o | o | Δ | x | x |

The solubility and low-temperature stability of general-pupose water-soluble polymers in detergents having the formulations shown in Table 3 were evaluated with the results shown in Table 3.

The evaluation standards for the solubility and low temperature stability are as follows. The low temperature stability was determined after storage at −5° C. for 1 week.

[Behavior of Dissolution]
 o: completely dissolved
 Δ: partially dissolved
 x: not dissolved

[Low-Temperature Stability]
 o: transparent liquid

EXAMPLE 4

Detergents having the formulations shown in Table 4 were evaluated with respect to softness with the results shown in Table 4.

The characteristic properties were evaluated as follows. Softness:

A hair bundle having a length of 20 cm and a weight of 20 g was immersed in hot water of 40° C., to which 1 g of a detergent composition was applied and lathered for 1 minute, followed by rinsing whereupon softness of the hair was evaluated by 10 panelers according to the following standards.
 o: soft Δ: fairly soft
x: not soft
Behaviors of dissolution and precipitation of quaternary nitrogen-containing cellulose ether:
0.5% of cationized cellulose was added to a 10% surface active agent solution, whereupon the behavior of dissolution and the behavior of precipitation when diluted to 1:10 were evaluated according to the following standards.
[Behavior of Dissolution]
  o: completely dissolved
  Δ: partially dissolved
  x: not dissolved
[Behavior of Precipitation]
  o: precipitated in large amounts
  Δ: partially precipitated
  x: not precipitated

EXAMPLE 5

The solubility of general-purpose water-soluble polymers in detergents having the formulations shown in Table 5 and the low temperature stability were evaluated with the results shown in Table 5.

The solubility and low temperature stability were evaluated according to the following standards.
[Behavior of Dissolution]
  o: completely dissolved
  Δ: partially dissolved
  x: not dissolved
[Low Temperature Stability]
  o: transparent liquid
  Δ: semi-transparent liquid
  x: precipitation

TABLE 4

| | | Sample No. | | |
|---|---|---|---|---|
| | | 15 | 16 | 17 |
| $C_{11}H_{23}CONHCH_2CH_2N\begin{array}{c}CH_2CH_2OH\\CH_2COOH.N(CH_2CH_2OH)_3\end{array}$ | (Synthetic Example 2) | 14.3 | — | — |
| $C_{11}H_{23}CONHCH_2CH_2N\begin{array}{c}CH_2CH_2OH\\CH_2COOH.NH_3\end{array}$ | (Synthetic Example 2) | — | 10.5 | — |
| $C_{11}H_{23}CONHCH_2CH_2N\begin{array}{c}CH_2CH_2OH\\CH_2COO.Na\end{array}$ | | — | — | 10.6 |
| Cationized Cellulose* | | 0.5 | 0.5 | 0.5 |
| Ion-exchanged Water | | balance | balance | balance |
| Properties | | | | |
| Softness | | o | o | Δ |
| Behavior of Dissolution | | o | o | o |
| Behavior of Precipitation | | o | o | Δ |

*Polymer JR400 (by UCC)

TABLE 5

| | | Sample No. | | | | | | | |
|---|---|---|---|---|---|---|---|---|---|
| | | 18 | 19 | 20 | 21 | 22 | 23 | 24 | 25 |
| $C_{11}H_{23}CONHCH_2CH_2N\begin{array}{c}CH_2CH_2OH\\CH_2COOH.N(CH_2CH_2OH)_3\end{array}$ (Synthetic Example 1) | | 43.0 | — | 14.3 | — | — | — | — | — |
| $C_{11}H_{23}CONHCH_2CH_2N\begin{array}{c}CH_2CH_2OH\\CH_2COOH.NH_3\end{array}$ (Synthetic Example 1) | | — | 34.5 | — | 10.5 | 10.5 | — | — | — |
| $C_{11}H_{23}CONHCH_2CH_2N\begin{array}{c}CH_2CH_2OH\\CH_2COO.Na\end{array}$ | | — | — | — | — | — | 31.9 | 10.6 | 10.6 |
| NaCl | | 0.99 | 0.99 | 0.33 | 0.66 | 0.66 | 0.99 | 0.17 | 0.17 |
| Methylcellulose | | — | — | 1 | 1 | — | — | 1 | — |
| Hydroxyethylcellulose | | — | — | — | — | 1 | — | — | 1 |
| Ion-exchanged Water | | balance | → | → | → | → | → | → | → |
| Behavior of Dissolution | | — | — | o | o | o | — | x | x |
| Low-temperature Stability | | o | o | o | o | o | x | x | x |

EXAMPLES 6-8

A shampoo, a wool or light duty detergent, and a detergent for dish washing of the following formulations, respectively, had low irriativeness against the skin with good detergency.

EXAMPLE 6

Shampoo:

$$C_{11}H_{23}CONHCH_2CH_2N\begin{array}{l}CH_2CH_2OH\\CH_2COOH\cdot N(CH_2CH_2OH)_3\end{array}$$

| | |
|---|---|
| (Synthetic Example 2) | 10 wt % |
| Polyoxyethylene (3.0) alkyl (12 carbon atoms on average) ether sulfate triethanolamine salt | 5 |
| Lauric acid diethanolamide | 1 |
| Perfume, colorant | suitable amounts |
| Water | balance |
| Total | 100 wt % (pH 7.2) |

EXAMPLE 7

Wool, Light Duty Detergent:

$$C_{11}H_{23}CONHCH_2CH_2N\begin{array}{l}CH_2CH_2OH\\CH_2COOH\cdot NH_3\end{array}$$

| | |
|---|---|
| (Synthetic Example 3) | 10 wt % |
| Lauryl dimethylamine oxide | 5 |
| Ethyl alcohol | 8 |
| Perfume | suitable amount |
| Water | balance |
| Total | 100 wt % |

EXAMPLE 8

Dish Wash Detergent:

$$C_{11}H_{23}CONHCH_2CH_2N\begin{array}{l}CH_2CH_2OH\\CH_2COOH\cdot N(CH_2CH_2OH)_3\end{array}$$

| | |
|---|---|
| (Synthetic Example 2) | 15 wt % |
| Triethanolamine alpha-olefinsulfonate (12 carbon atoms on average) | 5 |
| Lauric acid diethanolamide | 5 |
| Ethyl alcohol | 8 |
| Perfume, colorant, clouding agent | suitable amounts |
| Water | balance |
| Total | 100 wt % |

EXAMPLE 9

A anti-dandruff shampoo composition of the following formulation was found to have very weak irriativeness against the skin and a good dandruff-removing effect.

$$C_{11}H_{23}CONHCH_2CH_2N\begin{array}{l}CH_2CH_2OH\\CH_2COOH\cdot N(CH_2CH_2OH)_3\end{array}$$

| | |
|---|---|
| (Synthetic Example 2) | 10 wt % |
| Polyoxyethylene (3.0) alkyl (12 carbon atoms on average) ether sulfate triethanolamine salt | 5 |
| Lauric acid diethanolamide | 1 |
| Piractone Ohramine (Octopirox) | 1 |
| Ethyl alcohol | 2 |
| Perfume, colorant | suitable amounts |
| Water | balance |
| Total | 100 wt % |

EXAMPLE 10

A bath cleaner of the following formulation exhibited good detergency and could efficiently wash away soap scum deposited on a bath tub.

$$C_{11}H_{23}CONHC_2H_4N\begin{array}{l}C_2H_4OH\\CH_2COOH\end{array}$$

| | |
|---|---|
| (Synthetic Example 1) | 20 wt % |
| Sodium chloride | 0.15 |
| Citric acid | 0.7 |
| Water | balance |
| Total | 100 wt % |

EXAMPLE 11

Shampoo:

$$C_{11}H_{23}CONHCH_2CH_2N\begin{array}{l}CH_2CH_2OH\\CH_2COOH\cdot N(CH_2CH_2OH)_3\end{array}$$

| | |
|---|---|
| (Synthetic Example 2) | 10 wt % |
| Polyoxyethylene (3.0) alkyl (12 carbon atoms on average) ether sulfate triethanolamine salt | 5 |
| N—myristyl-beta-alanine.triethanolamine salt | 3 |
| Lauric acid diethanolamide | 1 |
| Cationized cellulose (Polymer JP400, UCC) | 0.25 |
| Perfume, colorant | suitable amounts |
| Water | balance |
| Total | 100 wt % |

EXAMPLE 12

Wool, Light Duty Detergent:

$$C_{11}H_{23}CONHCH_2CH_2N\begin{array}{l}CH_2CH_2OH\\CH_2COOH\cdot NH_3\end{array}$$

| | |
|---|---|
| (Synthetic Example 3) | 10 wt % |
| Sodium N—lauryliminodiacetate | 1 |
| Lauryldimethylamine oxide | 5 |
| Methyl cellulose | 0.5 |
| Ethyl alcohol | 8 |
| Perfume | suitable amount |
| Water | balance |
| Total | 100 wt % |

EXAMPLE 13

Dish Wash Detergent:

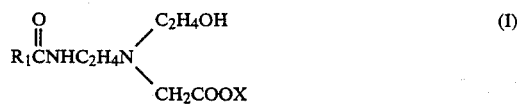

| | |
|---|---|
| (Synthetic Example 2) | 15 wt % |
| N—laurylaminopropionic acid triethanolamine salt | 5 |
| Alpha-olefinsulfonic acid triethanolamine salt (12 carbon atoms on average) | 5 |
| Lauric acid diethanolamide | 2 |
| Carboxyvinyl polymer (Carbopole 941, Goodrich Co., Ltd.) | 0.5 |
| Ethyl alcohol | 8 |
| Perfume, colorant, clouding agent | suitable amounts |
| Water | balance |
| Total | 100 wt % |

EXAMPLE 14

A anti-dandruff shampoo composition of the following formulation exhibited very weak irritativeness against the skin with a good dandruff-removing effect.

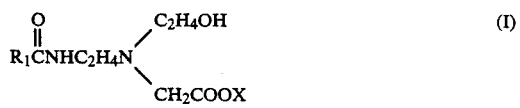

| | |
|---|---|
| (Synthetic Example 2) | 10 wt % |
| N—lauryl-beta-iminodipropionic acid triethanolamine salt | 2 |
| Polyoxyethylene (3.0) alkyl (12 carbon atoms on average) ether sulfate triethanolamine salt | 5 |
| Cationized cellulose (Polymer JR400, UCC) | 0.5 |
| Diethanolamide laurate | 1 |
| Piractone Ohramine (Octopirox) | 1 |
| Ethyl alcohol | 2 |
| Perfume, colorant | suitable amounts |
| Water | balance |
| Total | 100 wt % |

EXAMPLE 15

A bath cleaner of the following formulation had good detergency and could wash away soap scum deposited on a bath tub.

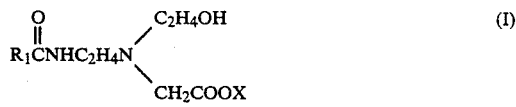

| | |
|---|---|
| (Synthetic Example 1) | 20 wt % |
| Sodium N—oleyl-iminodiacetate | 10 |
| Sodium chloride | 0.15 |
| Citric acid | 0.7 |
| Water | balance |
| Total | 100 wt % |

What is claimed is:

1. A detergent composition comprising as a main detergent active ingredient a secondary amidoamino acid or its salts of the following formula (I):

wherein $R_1$ represents an alkyl group, a hydroxyalkyl group, an aralkyl group or an alkenyl group each having from 7 to 23 carbon atoms, and X represents hydrogen, ammonium ion or a triethanolammonium ion; with the content of a water-soluble inorganic salt being 0.2 mol or less per 100 g of said secondary amidoamino acid, calculated as the acid type secondary amidoamino acid when the salts are used.

2. A liquid detergent composition, comprising:
   from 1 to 45 wt% of a secondary amidoamino acid or its salts of the formula (I):

$$\underset{R_1CNHC_2H_4N}{\overset{O}{\|}} \diagup \overset{C_2H_4OH}{\underset{CH_2COOX}{}} \qquad (I)$$

wherein $R_1$ represents an alkyl group, a hydroxyalkyl group, an aralkyl group or an alkenyl group each having from 7 to 23 carbon atoms, and X represents hydrogen, ammonium ion or a triethanolammonium ion, and from 0.05 to 10 wt% of a water-soluble polymer which is insoluble in a concentrated salt solution; the composition having a water-soluble inorganic salt content of not larger than 1 wt%.

3. A detergent composition, comprising:
   from 5 to 35 wt% of a secondary amidoamino acid or its salts of the following formula (I):

$$\underset{R_1CNHC_2H_4N}{\overset{O}{\|}} \diagup \overset{C_2H_4OH}{\underset{CH_2COOX}{}} \qquad (I)$$

wherein $R_1$ represents an alkyl group, a hydroxyalkyl group, an aralkyl group or an alkenyl group each having from 7 to 23 carbon atoms, and X represents hydrogen, ammonium ion or a triethanolammonium ion; with the content of a water-soluble inorganic salt being 0.2 mol or less per 100 g of said secondary amidoamino acid, calculated as the amidoamino acid when the salts are used, and from 1 to 17.5 wt% of an alkylamino acid-type surface active agent of the following formula (II):

$$R_2-N \diagup \overset{R_3}{\underset{(CH_2)_mCOOM}{}} \qquad (II)$$

wherein $R_2$ represents a saturated or unsaturated hydrocarbon group having from 8 to 20 carbon atoms, $R_3$ represents a hydrogen atom or $-CH_2-_m-COOM$ in which m is a value of from 1 to 4, and M represents hydrogen, an alkali metal ion, ammonium ion or an alkanolamine.

* * * * *